United States Patent [19]

McHardy

[11] Patent Number: 5,273,970
[45] Date of Patent: Dec. 28, 1993

[54] TREATMENT OF PROTOZOAL DISEASES

[75] Inventor: Nicholas McHardy, Berkhamsted, United Kingdom

[73] Assignee: Coopers Animal Health Limited, Hertfordshire, England

[21] Appl. No.: 635,822

[22] Filed: Jan. 3, 1991

[30] Foreign Application Priority Data

Jan. 5, 1990 [GB] United Kingdom ............... 9000241

[51] Int. Cl.$^5$ .................. A61K 31/505; A61K 31/65; A61K 31/255
[52] U.S. Cl. ................... 514/157; 514/155; 514/158; 514/272
[58] Field of Search ............ 514/155, 157, 158, 272

[56] References Cited

U.S. PATENT DOCUMENTS

| | | | |
|---|---|---|---|
| 3,969,520 | 7/1976 | Garzia | 514/272 |
| 4,587,342 | 5/1986 | Daluge et al. | 544/324 |
| 4,761,475 | 8/1988 | Daluge et al. | 544/324 |

FOREIGN PATENT DOCUMENTS

| | | |
|---|---|---|
| 0051879 | 5/1982 | European Pat. Off. |
| 0238207 | 2/1987 | European Pat. Off. |
| 236002 | 9/1987 | European Pat. Off. |
| 0384722 | 8/1990 | European Pat. Off. |
| 1372981 | 11/1974 | United Kingdom . |

OTHER PUBLICATIONS

Burchall and Hitchings, "Inhibitor Binding Analysis of Dihydrofolate Reductases from Various Species," Mol. Pharmacol. 1, 126–136 (1965).
Hitchings and Bushby Proc. 5th Int. Cong. Biochem., Section 7, Abstract 7.42.
The Merck Manual, 5th edition, p. 671, 1987.

Primary Examiner—Frederick E. Waddell
Assistant Examiner—K. Weddington
Attorney, Agent, or Firm—Nixon & Vanderhye

[57] ABSTRACT

The antibacterial substance baquiloprim (2,4-diamino-5-[8-dimethylamino-7-methyl-5-quinolylmethyl]pyrimidine) is shown to be active against protozoal infections, e.g. toxoplasmosis. Preferably the baquiloprim is administered together with a sulphonamide.

7 Claims, 1 Drawing Sheet

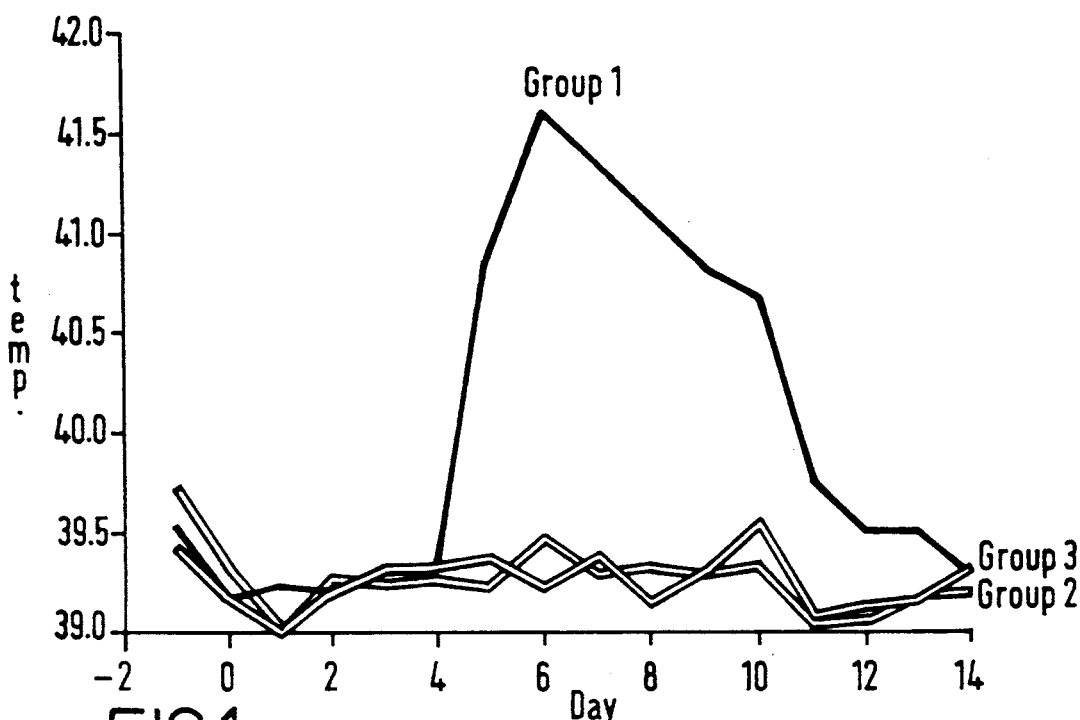
FIG.1. Mean febrile responses dosing with a combination of Baquiloprim and Sulphadimidine
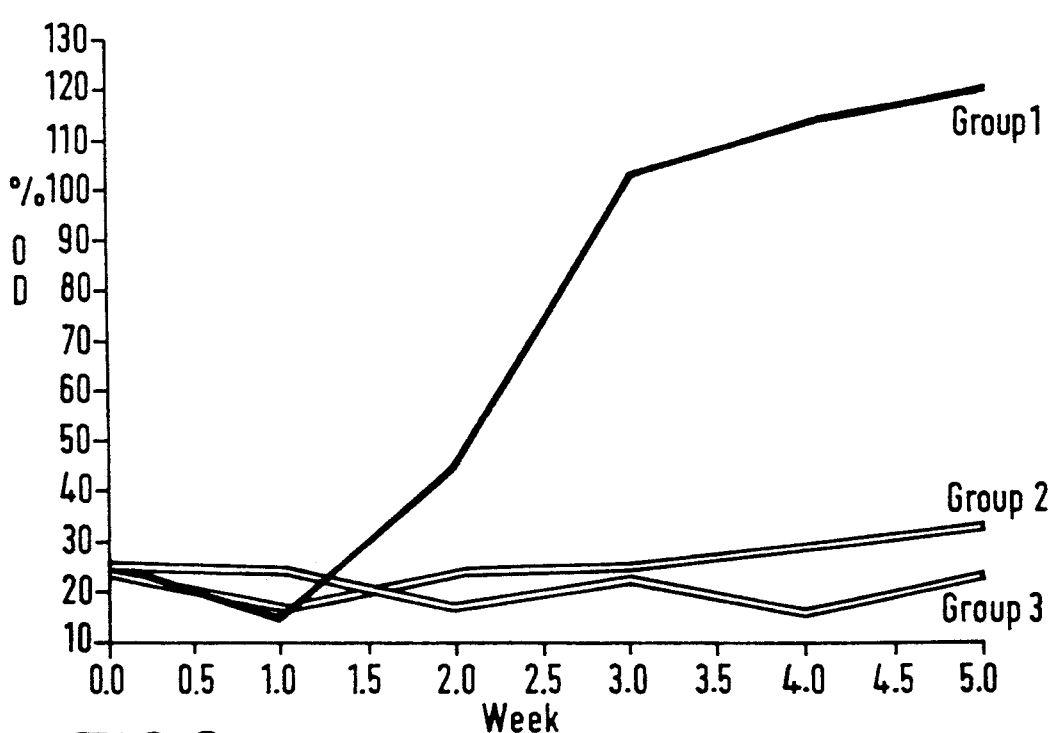
FIG.2. Mean serological responses following dosing with a combination of Baquiloprim and Sulphadimidine

TREATMENT OF PROTOZOAL DISEASES

The present invention relates to the treatment of protozoal diseases. More particularly, the present invention is concerned with the use of a 2,4-diamino-5-(substituted)pyrimidine in treating toxoplasmosis and the use of this compound for the manufacture of medicaments for the treatment of toxoplasmosis.

European Patent Specification 51879 discloses that 2,4-diamino-5-(substituted) pyrimidines of the formula (I):

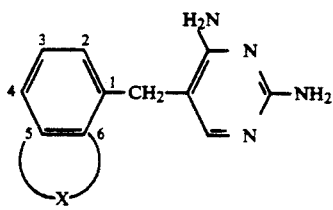

or salts, N-oxides or acyl derivatives thereof, wherein ($\bar{x}$) is a six membered ring optionally containing a hetero atom, both the phenyl ring and the ($\bar{x}$) being optionally substituted except that when ($\bar{x}$) does not contain a hetero atom either or both the phenyl ring or ($\bar{x}$) must be substituted other than solely by a hydroxy group at the 4-position of the phenyl ring, and, that there are no substituents attached to the atom of ($\bar{x}$) adjacent to the 6-position of the phenyl ring, have useful antibacterial activity, particularly against gram positive and negative aerobic bacteria. Baquiloprim (2,4-diamino-5-(8-dimethylamino-7-methyl-5-quinolylmethyl) pyrimidine) is a preferred compound exemplified in European Patent Specification 51879. The 2,4-diamino-5-(substituted) pyrimidines of European Patent Specification 51879 may advantageously be combined with a sulphonamide, in the case of baquiloprim it has been found that combination with sulphadimidine or sulfadimethoxine is preferred.

Parasitic protozoal infections are responsible for a wide variety of diseases of medical and veterinary importance, ranging across malaria and *Pneumocystis carinii* pneumonia in man and various coccidioses in birds, fish and mammals. Many of the diseases are life threatening to the host and cause considerable economic loss in animal husbandry. The Apicomplexa are a phylum of the sub-kingdom Protozoa and include the coccidians, (e.g. Toxoplasma) and the malaria parasite Plasmodium. We have now found that baquiloprim is active against protozoal infections and, in particular, against apicomplexan infections such as those caused by *Toxoplasma gondii*.

*Toxoplasma gondii* occurs in a wide range of mammals, e.g. cattle, sheep, pigs, horses, dogs, cats and humans, and birds, e.g. chickens. Infection frequently remains inapparent and latent but in certain circumstances it can give rise to an acute illness (toxoplasmosis) which is often fatal. Thus, for example *T. gondii* is associated with congenital toxoplasmosis of newborn children (probably the commonest form in humans) and with disease in immunocompromised hosts. Transplant patients treated with immunosuppressants may be at risk from infection with *T. gondii* parasites introduced in the donated organ. In another group of immumocompromised patients, those with Acquired Immune Deficiency Syndrome (AIDS), toxoplasmosis is associated with life-threatening encephalitis. Other immunocompromised patients at risk include those being treated with immunosuppressive drugs in cancer chemotherapy.

Infection with *T. gondii* during early pregnancy may lead to foetal death or abnormality, whilst congenital infection during late pregnancy is associated with eye disease which may subsequently appear in early adulthood. In animal husbandry *T. gondii* frequently gives rise to foetal death in pregnant sheep. Felids (including the domestic cat) are the definitive hosts of *T.gondii* and a common source of human toxoplasmosis, via infective stages in the faeces.

Toxoplasmosis may be controlled to a certain extent using pyrimethamine together with a sulphonamide. However, at the present time no effective treatment for toxoplasmosis is available.

BRIEF DESCRIPTION OF THE DRAWINGS

FIG. 1 is a graph plotting the change in temperature over a five week period for three groups of lambs showing the mean febrile response dosing with a combination of baquiloprim and sulphadimide, and FIG. 2 is a graph showing the mean serological responses to the same three groups over a five week period following dosing with a combination of baquiloprim and sulphadimide.

DESCRIPTION OF THE INVENTION

In a first aspect, the present invention provides the use of baquiloprim or a physiologically acceptable salt thereof for the treatment and/or prophylaxis of protozoal infections in animals (including humans).

In another aspect, the present invention provides the use of baquiloprim or a physiologically acceptable salt thereof for the manufacture of a medicament for the treatment and/or prophylaxis of protozoal infections in animals (including humans).

In a further aspect, the present invention provides a method of treating and/or preventing protozoal infections in animals (including humans) which comprises administering to the animal an effective amount of baquiloprim, or a physiologically acceptable salt thereof.

Suitably the protozoal infection is a sporozoal infection or an infection caused by *Pneumocystis carinii*. Preferably, the protozoal infection is an infection caused by *Toxoplasma gondii*.

Baquiloprim may be administered as the sole active agent to treat/control the protozoal infection but normally it will be coadministered with a sulphonamide. Suitable sulphonamides include:

Sulfanilamide, Sulfadiazine, Sulfamethisazole, Sulfapyridine, Sulfathiazole, Sulfamerazine, Sulfamethazine, Sulfisoxazole, Sulformethoxine, 2-(p-Aminobenzene)-sulfonamide-3-methoxypyrazine (Kelfizina), Sulfaingldianiline, Mafenide, 5-Sulfanilamido-2,4-dimethyl pyrimidine, 4-(N$^1$- Acetyl-sulfanilamido)-5,6-dimethoxy pyrimidine, 3-Sulfanilamido-4,5-dimethyl isoxazole, 4-Sulfanilamido-5-methoxy-6- decyloxy pyrimidine sulfamono-methoxine, 4-p-(8-Hydroxy quinolinyl- 4-azo)-phenyl-sulfanilamido-5,6-dimethoxy pyrimidine, Sulfadimeth- oxine, Sulfadimidine, Sulfamethaxozole Sulfamoxole, Sulfadoxine, Sulfaguanidine, Sulfathiodimethoxine, Sulfaquinoxaline, and p-(2- Methyl-8-hydroxyquinolinyl-5-azo)phenyl sulfanilamido-5,6-dimethoxy pyrimidine.

However, the most preferred combinations include those containing Sulfadiazine, Sulfamethoxazole, Sulfadimethoxine, Sulfadoxine, Sulfamoxole or Sulfadimidine.

Baquiloprim is a base and, as such, forms acid addition salts with acids. Suitable acid addition salts of baquiloprim include those formed with both organic and inorganic acids. Such acid addition salts will normally be pharmaceutically acceptable. Thus, preferred salts include those formed from hydrochloric, sulphuric, citric, tartaric, phosphoric, lactic, benzoic, glutamic, aspartic, pyruvic, acetic, succinic, fumaric, maleic, oxaloacetic, isethionic, stearic, fumaric, methanesulphonic, toluene p-sulphonic, lactobionic and glucuronic acids.

The compositions may be adapted for administration by routes well known to those skilled in the veterinary and formulation sciences. When baquiloprim is administered in conjunction with a sulphonamide, it is often convenient for one of these to be present as a salt, for example sodium sulphadimidine or an acid addition salt of the pyrimidine, for example formed from tactic, citric or formic acids, whilst the other component is present in free unsalted form (see for example UK patents 1176395, 1347472 and 1469521).

Baquiloprim, optionally in the presence of a sulphonamide, will normally be administered as a pharmaceutical composition for example one adapted for oral, parenteral, topical, intravaginal or intrarumenal administration.

Compositions suitable for oral administration include drenches (oral liquid dosing), which may be solutions or suspensions; tablets, boluses, pastes, or in-feed preparations in the form of powders, granules or pellets. Preferred orally administrable compositions include boluses.

Alternatively, the compositions may be adapted to be administered parenterally by sub-cutaneous, intramuscular or intravenous injection of a sterile solution or suspension, by implantation or as an intramammary injection whereby a suspension or solution is introduced into the udder via the teat.

Compositions suitable for topical administration include creams, ointments or sprays applied to the skin, and intravaginal compositions include pessaries, creams and foams.

For intrarumenal injection, the compositions of the invention may be solutions or solid or microcapsule suspensions. Typically the compositions are similar to the oral liquid preparations or parenteral preparations described herein. Such compositions are injected directly into the rumen, usually through the side of the animal, for example by a hypodermic syringe and needle or by an automatic injection device capable of giving single or multiple doses.

Pharmaceutically acceptable carriers present in the compositions of the present invention are materials recommended for the purpose of administering the medicament. These may be liquid, solid or gaseous materials, which are otherwise inert or medically acceptable and are compatible with the active ingredient.

For oral administration, fine powders or granules will contain diluting agents, for example lactose, calcium carbonate, calcium, phosphate, mineral carriers, etc., dispersing and/or surface active agents, for example polysorbates such as Tweens or Spans, and may be presented in a drench, in water or in a syrup, in a bolus, paste, or in a feed preparation, in capsules or sachets in the dry state or in a non-aqueous suspension, or in a suspension in water or syrup. Where desirable or necessary, preserving, suspending, thickening or emulsifying agents can be included. If intended for oral use, a bolus will be provided with retention means to inhibit regurgitation, for example it may be weighted with a heavy density material such as iron or tungsten or the like or may be retained by its shape, for example by wings which spring after administration. Boluses may contain disintegrating agents such as maize starch or calcium or sodium methyl celluloses, hydroxypropylmethyl cellulose, guar based vegetable gums, sodium alginates or sodium starch glycolates; granulating or binding agents such as starch in the form of mucilage, starch derivatives, such as "Snow Flake", cellulose derivatives such as talc, calcium stearate, methyl cellulose, gelatin or polyvinylpyrrolidone; and/or lubricating agents, such as magnesium stearate or stearic acid.

For parenteral administration, the compounds may be presented in sterile injection solutions which may contain antioxidants or buffers, or as injectable suspensions. Suitable solvents include water, in the case of suspensions, and organic solvents such as dimethylformamide, dimethylacetamide, diethylacetamide, ethyl lactate, ethyl akate, dimethylsulphoxide, alcohols, e.g. ethanol, glycols, e.g. ethylene glycol, propylene glycol, butylene glycol and hexamethylene glycol, polyethylene glycols containing 2 to 159 ethylene glycol monomer units and having average molecular weights from about 90 to 7500, glycerin formal, glycofurol, glycerol, isopropylmyristate N-methylpyrrolidone, 2-pyrrolidone polyethylene glycoethers of tetrahydrofurfuryl alcohol and diethylene glycol, and fixed and neutral oils, for example fractionated coconut oil. One formulation found to be particularly advantageous for intramuscular injection comprises an 18% 1:5 (pyrimidine:sulphonamide) suspension in fractionated coconut oil (Miglyol). This formulation has the advantage that it does not cause pain at the site of injection.

Other compounds which may be included are, for example, medically inert ingredients, e.g. solid and liquid diluents such as lactose, glucose, starch or calcium phosphate for tablets, boluses or capsules; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; dedusting agents such as liquid paraffin, fixed oils and surfactants and other therapeutically acceptable accessory ingredients such as humectants, preservatives, buffers, and antioxidants which are useful as carriers in such formulations.

When desired, other medicaments and/or nutrients such as vitamins or the like, may also be included.

Alternatively the active compound(s) may be presented in a pure form as an effective unit dosage, for instance, compressed as a tablet or the like.

The pharmaceutical compositions for administration of baquiloprim can be prepared by the admixture of baquiloprim with a pharmaceutically acceptable carrier. Other ingredients, for example, a sulphonamide or the conventional pharmaceutical excipients described above may be added as required.

The oral, parenteral and intrarumenal routes of administration are preferred.

The doses and ratios of the components of the composition are chosen such that there is provided at the site of infection a concentration of each component sufficient to exert a synergistic effect. In general the active ingredients are present in a ratio of between 1:1 and 1:20 baquiloprim:sulphonamide. Suitably, combinations for parenteral use are those having the ratio of approximately 1:5 baquiloprim:sulphonamide. For oral administration suitably the active ingredients are present in a ratio of between 1:4 and 1:10 pyrimidine:sulphonamide, preferably 1:9.

When administered parenterally, for example by intramuscular injection, the composition typically is administered at dosages of 10–30 mg/kg active ingredients wherein the ratio of pyrimidine:sulphonamide is approximately 1:5.

When administered orally to animals in a bolus formulation, a ratio of approximately 1:9 is preferred. A once-in-two-days formulation typically contains 1 mg/kg to 8 mg/kg of the baquiloprim, preferably approximately 4 mg/kg; and 9 mg/kg to 72 mg/kg of sulphonamide e.g. sulphadimidine, preferably approximately 36 mg/kg of sulphonamide. A once-in-four-days bolus formulation typically contains approximately 6 mg/kg to 16 mg/kg of baquiloprim, preferably approximately 8 mg/kg; and approximately 54 mg/kg to 144 mg/kg of sulphonamide e.g. sulphadimidine, preferably approximately 72 mg/kg of sulphonamide.

Bolus formulations will normally contain a unit dose of 0.5 g to 3 g of baquiloprim, for example about 0.8 g or 1.6 g of baquiloprim, and 5 g to 30 g of sulphonamide e.g. sulphadimidine, for example about 7.2 g or 14.4 g of sulphonamide.

The invention will now be illustrated in greater detail by means of examples.

EXPERIMENTAL PROCEDURES

1. Production of Toxoplasma Oocysts

Two 6-month old specific-pathogen-free cats were infected by feeding mouse brain homogenate containing approximately 1000 tissue cysts of *Toxoplasma gondii* M1 isolate. Faeces were collected from the cats between days 1 and 14 after infection and screened for Toxoplasma oocysts. Positive samples from 5 to 10 days after infection were selected and oocysts recovered by salt flotation. Oocysts were purified by differential centrifugation and allowed to sporulate by incubation in 2% $H_2SO_4$ for 3–4 days at 22° C. Sporulated oocysts were stored in 2% $HSO_4$ at 4° C. until required.

2. Experimental Design

Two groups, each of 15 Toxoplasma seronegative greyface or Dorset one-year-old ewe lambs, were housed in pens. An additional six lambs were distributed equally through the groups as "temperature controls" (Table 1).

Serum samples were stored at −20° C. until required for testing for Toxoplasma antibody by ELISA (Buxton D et al (1988) Journal of Comparative Pathology, 98, 225–236) as one batch at the end of the trial.

3. Experimental Infection with Toxoplasma

Stored oocysts in 2% $H_2SO_4$ were washed and resuspended in water to give an estimated 1000 sporulated oocysts/ml. All 30 animals in groups 1 and 2 were each inoculated by stomach tube with 1 ml of oocyst suspension flushed down by 15 ml of water.

Replicate oocyst counts on samples of inoculum gave a mean count of 1000 sporulated oocysts/infective dose.

4. Medication 15 g Boluses were used containing 0.8 g baquiloprim (BQP) and 7.2 g sulphadimidine (SDD). One half of one bolus was given orally to each ewe lamb in group 2 on day 2 and again, 30 hours later, on day 3.

As the boluses were larger than ideal for oral dosing of sheep each animal was orally dosed with 60 ml of water immediately after each bolus was given, to reduce the risk of regurgitation or choking. Furthermore, all animals stood on clean concrete after each dosing for 30 minutes before being returned to their pens so that any regurgitated boluses might be spotted. In the event no choking or regurgitation occurred.

i) FEBRILE RESPONSE

All infected lambs in group 1 showed a clear febrile response between day 5 and day 10 after infection. The non-infected temperature controls (group 3) did not show any abnormal temperature responses (FIG. 1).

BQP/SDD treated ewe lambs (group 2): Rectal temperatures of all ewe lambs remained within the normal range at all times with the exception of one animal on one day.

ii) SEROLOGICAL RESPONSE

Sera were tested using an ELISA designed to detect specific anti-Toxoplasma IgG in sheep. After correction for plate variation results were calculated by expressing the optical density of a test sample as a percentage of the optical density of the laboratory's standard positive control serum.

With this assay a percentage value of 25 or less in adult sheep is taken to be negative whereas a value rising above this is normally taken to indicate that the animal in question has had prior experience of *Toxoplasma gondii*. Cross reactions with other protozoa of sheep is probably the reason for the seemingly high background which has to be tolerated with all Toxoplasma serological tests.

The mean serological responses in each of the three groups are shown in FIG. 2.

CONCLUSIONS

1. Temperatures in the non-infected temperature controls (group 3) remained normal throughout the trial and the same animals did not develop antibody to *T.gondii* during the trial. This indicates that groups 1 to 3 were not exposed to environmental conditions that might alter their core temperatures. In addition, there is no evidence to suggest that they were exposed to "wild" *T.gondii* infection that theoretically can contaminate livestock feed and bedding from unidentified, uncontrolled sources.

2. The non-medicated lambs (group 1) showed the expected febrile and serologicel responses to infection with Toxoplasma. This verified that the challenge inoculum contained viable *T.gondii* at the correct dose level and that it was given by the correct route.

3. Oral medication with BQP/SDD prevented the expected febrile response (only one animal developed a temperature greater than 41° C. and for one day only) and virtually abolished serologicel responses to *T.gondii*. The magnitude of the effect was highly significant and indicates that BQP/SDD had a major effect in suppressing *T.gondii* from establishing in the animals. The observation that 3 ewe lambs did produce antibody to Toxoplasma over a number of weeks shows that while clinical signs of infection were prevented a very low degree of subclinical infection became established in a minority of the group.

4. In this particular trial BQP/SDD was highly effective and clearly has activity, against Toxoplasma.

TABLE 1

Details of experimental groups.

| Group | No. sheep Greyface | No. sheep Dorset | Total | Mean body weight (kg) (% standard error) |
|---|---|---|---|---|
| 1 | 6 | 9 | 15 | 54.6 (1.3) |
| 2 | 7 | 8 | 15 | 54.6 (1.7) |
| 3 | 5 | 1 | 6 | 55.7 (1.8) |

Rectal temperatures of all 36 sheep were recorded daily from before infection until day 14 after infection. All these groups were treated as shown in Table 2. Blood samples were collected from all 36 sheep before infection and weekly for 5 weeks from infection

TABLE 2

Dosing regime.

| Day | Treatment 0 | Treatment 2 | Treatment 3 |
|---|---|---|---|
| Group 1 | Toxo | — | — |
| Group 2 | Toxo | BQP/SDD | BQP/SDD |

TABLE 2-continued

Dosing regime.

| Day | Treatment 0 | Treatment 2 | Treatment 3 |
|---|---|---|---|
| Group 3 | — | — | — |

Toxo = 1,000 sporulated M1 oocysts orally
BQP/SDD = baquiloprim/sulphadimidine. ¼ bolus orally each.

I claim:

1. A method of treating a *Toxoplasma gondii* infection in a non-human animal or human subject which comprises administering to the said subject an anti-protozoal effective amount of baquiloprim or a physiologically acceptable salt thereof.

2. A method as claimed in claim 1 wherein the baquiloprim or physiologically acceptable salt thereof is administered in the form of a bolus.

3. A method as claimed in claim 1 wherein the baquiloprim or physiologically acceptable salt thereof is coadministered with a sulphonamide.

4. A method as claimed in claim 3 wherein the sulphonamide is sulfadiazine, sulfamethoxazole, sulfadoxine or sulfamoxole.

5. A method as claimed in claim 3 wherein the sulphonamide is sulfadimethoxine.

6. A method as claimed in claim 3 wherein the sulphonamide is sulfadimidine.

7. A method as claimed in claim 3 wherein the baquiloprim or physiologically acceptable salt thereof and the sulphonamide are administered in the form of a bolus.

* * * * *